(12) United States Patent
Parker

(10) Patent No.: US 6,321,100 B1
(45) Date of Patent: Nov. 20, 2001

(54) REUSABLE PULSE OXIMETER PROBE WITH DISPOSABLE LINER

(75) Inventor: Brent Parker, Murrieta, CA (US)

(73) Assignee: Sensidyne, Inc., Clearwater, FL (US)

( * ) Notice: Subject to any disclaimer, the term of this patent is extended or adjusted under 35 U.S.C. 154(b) by 0 days.

(21) Appl. No.: 09/352,144

(22) Filed: Jul. 13, 1999

(51) Int. Cl.[7] .................................................. A61B 5/00
(52) U.S. Cl. ................................... 600/344; 600/340
(58) Field of Search .................................. 600/310, 322, 600/323, 340, 344

(56) References Cited

U.S. PATENT DOCUMENTS

| Re. 36,000 | 12/1998 | Swedlow et al. . | |
|---|---|---|---|
| 4,621,643 | 11/1986 | New, Jr. et al. . | |
| 4,685,464 | 8/1987 | Goldberger et al. . | |
| 4,700,708 | 10/1987 | New, Jr. et al. . | |
| 4,830,014 | 5/1989 | Goodman et al. . | |
| 5,090,410 | 2/1992 | Saper et al. . | |
| 5,094,240 | 3/1992 | Muz . | |
| 5,170,786 | 12/1992 | Thomas et al. . | |
| 5,437,275 | * 8/1995 | Amundsen et al. | 600/323 |
| 5,507,286 | 4/1996 | Solenberger . | |
| 5,619,992 | * 4/1997 | Guthrie et al. | 600/323 |
| 5,673,693 | 10/1997 | Solenberger . | |
| 5,678,544 | 10/1997 | DeLonzor et al. . | |
| 5,817,010 | 10/1998 | Hibl . | |

* cited by examiner

Primary Examiner—Eric F. Winakur
(74) Attorney, Agent, or Firm—Jim Zegeer

(57) ABSTRACT

A reusable pulse oximeter sensor and disposable liner, comprising (a) a reusable pulse oximeter probe assembly including at least one light emitting diode and one photocell detector wherein said detector and emitter are mounted in plastic finger clip housing arms; and (b) at least one disposable foam strip having an aperture or apertures therein; and wherein the foam strip or strips have plastic modular receptacle which can matedly and removably engage the finger-clip housing arms and transmit and receive light through the apertures in foam strip or strips and through the appendage of a patient.

3 Claims, 2 Drawing Sheets

REUSABLE PULSE OXIMETER PROBE WITH DISPOSABLE LINER

BACKGROUND OF THE INVENTION

Heretofore the use of pulse oximeter finger probes has been limited to the use of a costly reusable probe, which is available in only one size, and is contaminated by use on a patient, or cheaper, single-use probes, which, in the aggregate, amount to a considerable expenditure for a health care institution. The present invention relates to a method of making and affixing a reusable finger probe to a patient by means of a finger clip apparatus with a disposable liner insert so that there is no contact between the costly, reusable portion of the probe and the patient. The contaminated liner, which is relatively inexpensive, can then be discarded after single patient use and the probe and finger clip can be re-used with a new liner. Additionally, such disposable inserts may be provided of different sizes and would greatly enhance the fit and function of the finger clip on the patient. This is important for several reasons. Firstly, a fitted finger clip would be much more comfortable to wear than conventional finger clips. Secondly, a fitted finger clip would allow the transmission and reception of infrared light from the LEDs of the probe without interference from extraneous light sources around the front and edges of the finger, and thirdly, a fitted finger clip would evenly distribute the pressure from the spring of the finger clip and would be much less likely to restrict blood flow to the digit and thereby cause erroneous oxygen saturation readings.

THE PRESENT INVENTION

The present invention not only solves the problems outlined above, but offers an alternative that is cheap to manufacture and easy to use.

In detail, the present invention is a method for improving the reusability, fit, and cleanliness of a reusable pulse oximeter finger sensor. It comprises a reusable pulse oximeter probe with at least one light emitting diode and one photocell detector wherein said emitter and detector are mounted in respective finger clip housing arms having apertures therein, one housing arm having an aperture aligned with said emitter, and the other housing arm having an aperture aligned with said detector. Incorporated into each opposing side of the finger clip is a T-shaped channel or slot with a locking protrusion or detent at the entrance of each of the channels. Also included is a disposable foam liner which is an initially, substantially planar, foam strip, having plastic backing on at least a part thereof and two T-shaped protrusions mounted in the lateral plane of said plastic backing. At opposing ends of the foam strip, and incorporated into the T-shaped protrusions, are notched levers for locking the foam strip into position in the T-shaped channel of the finger clip. In the center of the foam strip, the plastic backing is of a thickness that will allow it to bend into a "U" shape for insertion into the finger clip. Alternatively, the plastic backing may be entirely absent and the inherent flexibility of the foam itself will allow it to bend into the desired shape. Additionally, the foam strip contains two apertures located centrally therein containing silicone windows, or windows of another radiation transparent material, that will allow for the transmission and reception of infrared light. Additionally, the foam may also contain an adhesive for helping to adhere the finger clip to the patient.

Finally, and in a preferred embodiment of the invention, the finger clip may be of scaled down design and would allow for the insertion of different sizes of molded foam that would conform in size to the digit on which the finger clip is to be used. In such an application, the foam itself would be intended to substantially envelop the finger and the finger clip would be a mechanism for pinching or biasing the two foam halves together.

DESCRIPTION OF THE DRAWINGS

The above and other advantages of the invention will become more clear when considered with the following specifications and accompanying drawings wherein.

DESCRIPTION OF THE REUSABLE PULSE OXIMETER PROBE

Figure 1:
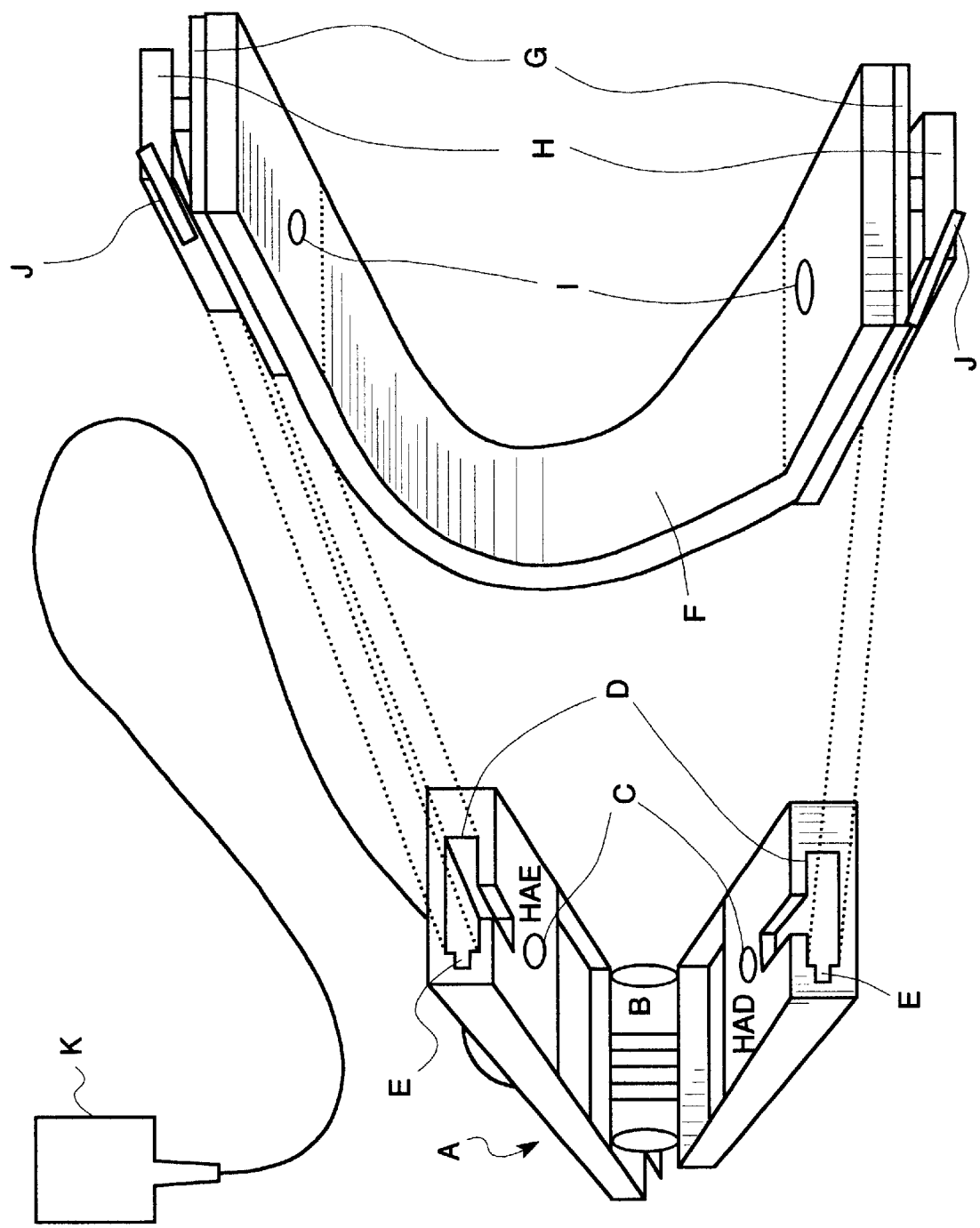
FIG. 1 is an exploded view of a standard pulse oximeter probe and finger clip with disposable liner.

The Reusable Pulse Oximeter Sensor constitutes a finger clip style pulse oximeter probe shown as FIG. 1, Item A. The probe incorporates two plastic housing arms, each housing arm containing apertures therein, said apertures shown as FIG. 1, Items C. One housing (HAE) contains the light emitting diode of the probe, and the other (HAD) contains the photocell detector. The emitter and detectors are aligned with the apertures of said housings in order to transmit and receive light through a human appendage. The housings are held together by a pin incorporating a spring, FIG. 1, item B, which inclines the two housings toward each other and clamps the apparatus on a human digit.

Within each housing is a "T" shaped channel, FIG. 1, item D, with a locking notch at the entrance thereof, said notch shown as FIG. 1, items E. The purpose of the channel and notch is to slidably engage the disposable liner of the finger clip and to lock it into its appropriate position within the finger clip. The probe is attached to a pulse oximeter through a connector, FIG. 1, item K. The above description constitutes the Reusable Pulse Oximeter Probe component of the invention.

DESCRIPTION OF THE DISPOSABLE LINER OR SHIELD

The components of the disposable liner or shield include an initially planar foam strip shown as FIG. 1, item F, incorporating two apertures, centrally located within the strip, and shown as FIG. 1, Items I, Each aperture has a diameter sufficient in size to accommodate the transmission and reception of light from a light emitting diode and photocell detector of the reusable pulse oximeter probe. Each aperture has a silicone window, or window of another material, which will allow for the transmission and reception of infrared light therethrough.

On either end of the foam strip there is a thin plastic backing, FIG. 1, items G, having a "T" shaped protrusion mounted in the lateral plane thereof and shown as FIG. 1, item H. The purpose of the "T" shaped protrusion is to slidably engage the "T" shaped channel of the reusable sensor, FIG. 1, item D, and to lock into place by means of the locking levers, FIG. 1, items J, a releasable detent.

Figure 2:
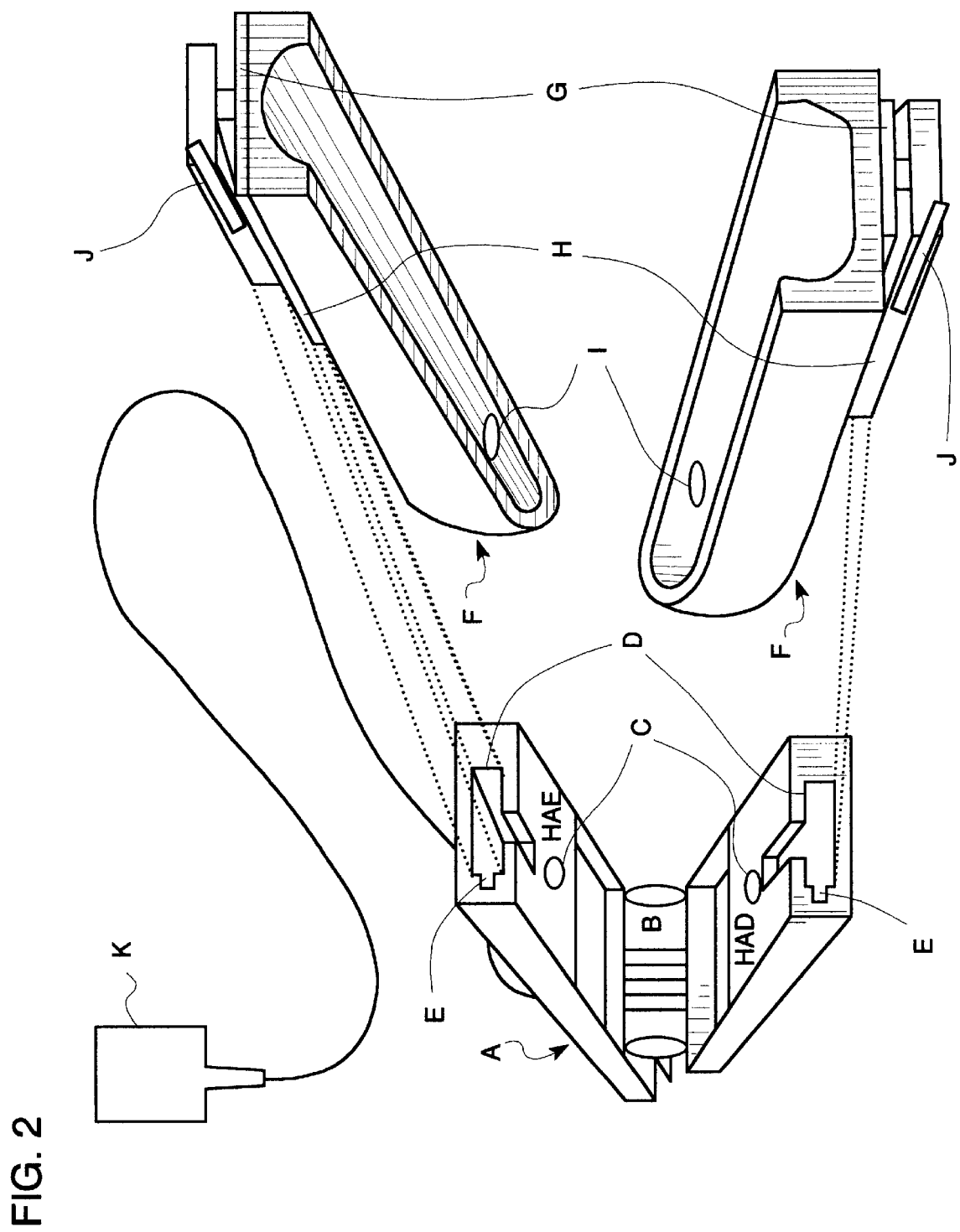
FIG. 2 is an exploded view of the preferred embodiment of the invention incorporating two disposable liners having finger conformance.

In the preferred embodiment of the invention, there are two disposable foam liners, with finger-shaped indentations therein, said indentations varying in size depending on the size of the patient's digit on which they are intended to be used. In this embodiment, the foam liners, FIG. 2, items F, have a plastic backing, FIG. 2, items G. The plastic backings have "T" shaped protrusions mounted thereon, FIG. 2, items H, which slidably engage the "T" shaped channel of the finger clip, FIG. 2, items D, the locking levers, FIG. 2, items J, engaging the locking notches of the finger clip, FIG. 2, items E, and securing the foam into place.

Other Fastening Means

As can be appreciated there are many ways of attaching the Disposable Liner or Shield to the Reusable Pulse Oximeter Probe. The above description describes attachment of the Disposable Liner to the Reusable Pulse Oximeter Probe by way of a modular type sliding connector. In addition to this means a number of other methods may be used including, hook and loop material, snap-on connectors, and removable adhesive.

What is claimed is:

1. In a spring clip oximeter probe having an emitter housing arm and a sensor housing arm which are biased towards each other at a predetermined pressure to grasp a portion of a living human body through which blood flows, an oximeter emitter mounted in said emitter housing arm to emit radiation into said portion of the living body and a radiation sensor mounted in said sensor housing arm for sensing radiation which passes through said portion of a living body, the improvement comprising a disposable safety shield detachably mounted on each of said housing arms, said safety shield having a radiation transparent window means isolating said emitter and sensor from said living body wherein each housing arm has a slot juxtaposed at the sides of said emitter and sensor, respectively, and said disposable shield having a slot engaging member at the respective ends thereof adapted to be received in said slot juxtaposed at the sides of said emitter and sensor, for receiving an end of said shield.

2. A disposable liner for use with a reusable pulse oximeter probe assembly including at least one light emitting diode and one photocell detector wherein said detector and emitter are mounted in plastic finger clip housing arms, said disposable liner comprising:

a disposable adhesive bandage including a disposable foam strip having a pair of apertures therein and modular receptacles carried on said foam strip, one over each aperture, respectively, wherein said modular receptacles can matedly and removably receive respective ones of said finger clip housing arms and transmit and receive light through the apertures of said foam strip and through an appendage of a patient.

3. The disposable bandage defined in claim 2 wherein said modular receptacle includes a channel with a locking member.

* * * * *